United States Patent [19]

Hsiao

[11] Patent Number: 5,009,894
[45] Date of Patent: Apr. 23, 1991

[54] ARRANGEMENT FOR AND METHOD OF ADMINISTERING A PHARMACEUTICAL PREPARATION

[75] Inventor: Charles Hsiao, Copper City, Fla.
[73] Assignee: Baker Cummins Pharmaceuticals, Inc., Miami, Fla.
[21] Appl. No.: 227,904
[22] PCT Filed: Mar. 7, 1988
[86] PCT No.: PCT/US88/00868
§ 371 Date: May 11, 1988
§ 102(e) Date: May 11, 1988
[51] Int. Cl.⁵ .............................. A61K 9/52
[52] U.S. Cl. ........................ 424/451; 206/532; 206/534; 206/540; 206/634; 424/468
[58] Field of Search .......... 424/468, 451; 215/32; 206/634, 532, 534, 540; 428/34.1

[56] References Cited

U.S. PATENT DOCUMENTS

| | | | |
|---|---|---|---|
| 2,134,489 | 10/1938 | Scherer | 221/60 |
| 2,968,391 | 1/1961 | Sparks | 206/42 |
| 3,503,493 | 3/1970 | Nagy | 206/56 |
| 3,741,384 | 6/1973 | Cloud | 206/56 AA |
| 4,155,454 | 5/1979 | Ryden | 206/532 |
| 4,209,096 | 6/1980 | Carkhuff | 206/621 |
| 4,212,918 | 7/1980 | Marquisee | 428/403 |
| 4,294,361 | 10/1981 | Margulies et al. | 206/532 |
| 4,353,869 | 10/1982 | Guth | 215/32 X |
| 4,357,192 | 11/1982 | Moser | 156/252 |
| 4,478,658 | 10/1984 | Wittwer | 156/69 |
| 4,493,574 | 1/1985 | Redmond et al. | 206/634 X |
| 4,506,793 | 3/1985 | MacGregor et al. | 215/32 |
| 4,525,339 | 6/1985 | Behl et al. | 424/462 X |
| 4,600,577 | 7/1986 | Didriksen | 424/462 |
| 4,859,469 | 8/1989 | Baudier et al. | 424/462 |

FOREIGN PATENT DOCUMENTS

| | | |
|---|---|---|
| 18054 | 2/1972 | Australia . |
| 26118 | 9/1972 | Australia . |
| 0467192 | 1/1975 | Australia . |
| 34651 | 10/1979 | Australia . |
| 1327208 | 4/1963 | France . |
| 2198461 | 3/1974 | France . |
| 2034662 | 6/1980 | United Kingdom . |
| 2134785 | 8/1984 | United Kingdom | 424/462 |

OTHER PUBLICATIONS

J. McGinity, Improved Method for Microencapsulation of Soluble Pharmaceuticals, Journal of Pharmaceutical Sciences, vol. 64, No. 5, May 1975, pp. 889-890.
C. A. Finch, Polymers for Microcapsule Walls; Chemistry and Industry, Nov. 18, 1985, pp. 752-756.

Primary Examiner—Thurman K. Page
Attorney, Agent, or Firm—Kirschstein, Ottinger, Israel & Schiffmiller

[57] ABSTRACT

A multitude of non-tacky coated pellets containing a pharmaceutical preparation is housed within a breakable packet which, when broken, enables ready removal of the pellets for the oral administration of the preparation to a patient. The packet includes a bendable backing sheet and a fracturable covering member between which the pellets are held in a vacuum-sealed environment prior to use. The coating of the pellets also prevents dissolution of the preparation in the mouth to avoid the sensation of bitter medicinal taste.

21 Claims, 1 Drawing Sheet

ARRANGEMENT FOR AND METHOD OF ADMINISTERING A PHARMACEUTICAL PREPARATION

BACKGROUND OF THE INVENTION

1. Field of the Invention

This invention generally relates to an arrangement for, and a method of, administering a pharmaceutical preparation and, more particularly, to the administration of an orally active pharmaceutical preparation contained in non-tacky coated pellets by breaking open a frangible packet containing the pellets, and by pouring the pellets from the opened packet into a human or animal patient's mouth.

2. Description of Related Art

Pharmaceutical preparations are traditionally orally administered to patients in many forms. Tablets are often used, but are not altogether desirable in certain cases. For example, depending on their size and coating, tablets can be difficult for certain patients, particularly children or small animals, to swallow. In some instances, the tablets begin to dissolve immediately upon coming into contact with saliva in the mouth, causing the unpleasant taste of the medicinal preparation to be sensed. In addition, relatively small tablets can be easily concealed or stolen. This is a particular importance in the administration of methadone and like drugs to narcotic addicts, or other medications to mental patients, because such patients may sometimes not swallow the tablets, but, instead, conceal them in their mouths or clothing in order to sell or dispose of the medication.

Capsules are also commonly used, particularly in those cases where slow or sustained release of the pharmaceutical preparation is desired. Although generally satisfactory for their intended purpose, capsules which enclose the pharmaceutical preparation within a gelatin container are generally larger in size than tablets and, hence, aggravate the swallowing problem. To overcome this problem, some patients break open the capsules to swallow the pharmaceutical preparation within the gelatin container, but often the pharmaceutical preparation has a bitter taste. In any event, the breaking open of a gelatin container can be messy and cause loss of part of the dosage amount.

Liquid pharmaceutical formulations are also generally satisfactory, but often need to be refrigerated or shaken prior to use. In some instances, such as certain pediatric antibiotic suspensions, preparation of the liquid formulations require addition of water to a powder immediately prior to use. Unless measuring spoons or the like are used, the dosing of the liquid formulation may be inaccurate, and spillage is a frequent problem, particularly with children. Also, liquid formulations often contain sweeteners, coloring and flavoring agents and other additives, many of which are not acceptable to nutrition-minded patients. Liquid formulations are also not stable for lengthy periods.

Another common problem with pharmaceutical preparations in tablet or capsule form is that there is very little room, if any, to print indicia on the tablet or capsule itself. Such indicia could be very useful if they identified the preparation itself, the dosage amount, the expiration date, or provided warning notices or directions for use. To meet this need, some drug manufacturers will design a tablet with a characteristic shape or color, or imprint an identifying mark on the tablet. However, no room exists on the tablet itself for more printed information and, generally, this information would be provided on a bottle or other relatively large-sized container housing the individual tablets or capsules.

However, such large-sized bottles or containers are generally too large to fit in one's pocket and, rather than being carried about, are generally stored in one's medicine cabinet and thus are out of sight of the patient when the tablet/capsule is being orally taken. In the case where a patient takes multiple medications, the medications are often co-mingled in a pill box or similar unmarked container, whereby the medications can be identified, if at all, only by their size, shape and color and reference to a pharmaceutical text. Elderly patients, especially, may become confused when unmarked medications are present in an unmarked holder, and may possibly take the wrong medication at the wrong time or exceed their recommended dosage of a given medication.

SUMMARY OF THE INVENTION

1. Objects of the Invention

It is a general object of this invention to provide a novel arrangement for administering pharmaceutical preparations which avoids the aforementioned drawbacks inherent in tablet, capsule or liquid formulations.

It is another object of this invention to provide an easily-openable packet containing the pharmaceutical preparation for prompt dispensing of the preparation.

A further object of this invention is to provide a miniaturized, frangible packet small enough to be easily carried in one's pocket and large enough to bear indicia identifying, e.g., the pharmaceutical preparation, the dosage, the expiration date, warning notices, and use instructions.

Yet another object of this invention is to provide pharmaceutical preparations in the form of coated pellets which are easy to swallow or to combine with liquids or foods for oral ingestion.

Still another object of this invention is to provide the coated pellets with non-tacky coatings to prevent the pellets from adhering to one another or to their container during manufacturing, storage and/or use.

A still further object of this invention is to orally administer the pellets while concealing the taste of the pharmaceutical preparation contained therein.

Another object of this invention is to substantially prevent the pellets from dissolving immediately upon entry into a patient's mouth, yet provide for easy dissolution in the stomach for quick absorption into the bloodstream.

Yet another object of this invention is to administer the pharmaceutical preparation to persons of all ages, e.g., pediatric or geriatric patients, and to animals.

An additional object of this invention is to provide a novel form for pharmaceutical preparations administered to drug addicts and psychiatric patients which will substantially prevent theft or concealment of the medications.

Still another object of this invention is to provide a normally-sealed packet which, once its seal is broken, cannot be re-sealed, thereby preventing tampering with the medication.

Another object of this invention is to provide a readily disposable pellet-containing packet.

A further object of this invention is to provide a novel method of administration of a pharmaceutical preparation which is easy to swallow, inexpensive to manufacture, and convenient to use.

2. Features of the Invention

In keeping with these objects, and others which will become apparent hereinafter, one feature of this invention resides, briefly stated, in an arrangement for, and a method of, administering one or more dosage units of a pharmaceutical preparation which comprises a multitude of pellets containing the pharmaceutical preparation contained in a breakable packet. The breakable packet includes a backing sheet, preferably constituted of a paper material, and a covering member, preferably constituted of a synthetic plastic material and overlying the backing sheet. The covering member and backing sheet together bound a compartment in which the pellets are contained. The pellets have non-tacky coatings to prevent them from adhering to one another and to the packet. The packet has a frangible zone which, when broken, enables removal of the pellets from the compartment.

In use, the backing sheet is bendable when subjected to external forces, e.g., moderate fingertip pressures, at the frangible zone. When the backing sheet is bent, the covering member fractures at the frangible zone into fractured parts whereby an opening in the compartment is created, permitting removal of the pellets. The fractured parts remain on the bent backing sheet for ease of disposal.

Preferably, the covering member includes a hollow main portion having a predetermined cross-section, a neck portion having a cross-section less than said predetermined cross-section, and a flange portion sealed and attached to one major surface of the backing sheet. In the preferred embodiment, the frangible zone extends across the neck portion and, when the covering member fractures at the neck portion, walls are formed at the neck portion which bound a tapered pouring spout or funnel through which the pellets pass.

An opposite major surface of the backing sheet is advantageously applied with indicia to identify the pharmaceutical preparation itself, the dosage amount, the expiration date, and can provide warning notices or use instructions, as desired.

The covering member is preferably constituted of a light-transmissive material to permit viewing of the pellets through the covering member. In this way, a user can verify the extent to which the pellets have been removed from the packet.

Another feature of this invention resides in providing a non-tacky coating for each medication-containing pellet, said coating comprising a polymeric material, e.g., a cationic copolymeric acrylate resin based on methacrylate and neutral methacrylic acid esters. The coating further includes a basic compound filler that is soluble in acid. Any organic or inorganic compound having a high solubility rate in an acidic medium such as gastric juices may serve as the basic compound filler. As preferred embodiments, the filler may be calcium carbonate, aluminum hydroxide or magnesium carbonate, or any mixture thereof.

In use, the pellet coating surrounding the pharmaceutical preparation prevents the latter from being dissolved upon contact with saliva in a patient's mouth and, instead, delays such dissolution until the pellets reach the gastric juices in the patient's stomach. The basic compound dissolves in the acidic gastric juices and liberates the pharmaceutical preparation. Thus, the basic compound filler may be used in an amount sufficient to facilitate the desired release characteristics of the preparation. Typically, the filler is present in the coating in an amount from about 10% to about 90% by weight.

The polymeric material is advantageously selected from the group consisting of cellulosic, polyacrylate and polyvinyl alcoholic polymers.

A single packet may contain one or more compartments, each containing a fraction of a recommended dose to be administered to a patient. Likewise, multiple packets representing multiple doses can be provided on a common backing sheet or on a roll, and can be detached from the roll as required in order to allow precise dosages to be administered to the patient.

The average size of each pellet is generally not greater than 1 mm in diameter.

The novel features which are considered as characteristic of the invention are set forth in particular in the appended claims. The invention itself, however, both as to its construction and its method of operation, together with additional objects and advantages thereof, best will be understood from the following description of specific embodiments when read in connection with the accompanying drawings.

DETAILED DESCRIPTION OF THE PREFERRED EMBODIMENTS

Figure 1:
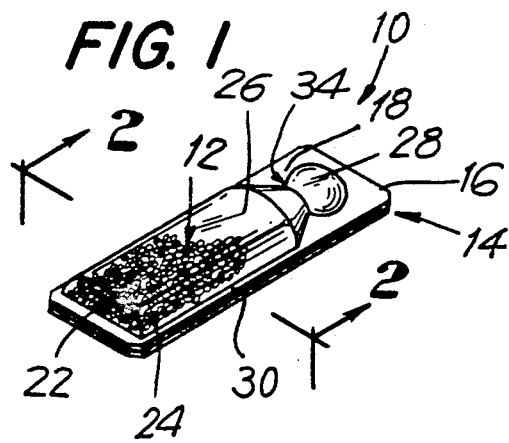
FIG. 1 is a front perspective view of an arrangement for administering a pharmaceutical preparation in accordance with this invention.
Figure 2:
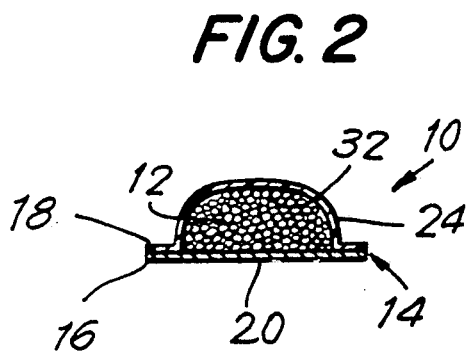
FIG. 2 is an enlarged cross-sectional view taken on line 2—2 of FIG. 1.

Referring now to FIGS. 1 and 2, reference numeral 10 generally identifies an arrangement for administering a pharmaceutical preparation. The arrangement 10 comprises a multitude of pellets, a representative one 12 of which is shown in enlarged sectional view in FIG. 3. The pellets 12 contain the pharmaceutical preparation to be administered to a patient.

The arrangement 10 further comprises a breakable packet 14 for holding the pellets 12. The packet includes a backing sheet 16, preferably constituted of a paper material, although vinyl and other thin, flexible sheeting materials may be utilized. The backing sheet generally, although not necessarily, lies in a plane and has opposite major surfaces, namely, top surface 18 and bottom surface 20. The paper material of the backing sheet renders the same bendable, and provides a certain degree of frangibility.

The packet 14 further includes a covering member 22, preferably constituted of a synthetic plastic material which is light-transmissive. The covering member 22 includes a hollow main portion 24 having a predetermined half-cylindrical cross-section, a neck portion 26 having a half-frusto-conical cross-section less than said cross-section of main portion 24, a head portion 28 having a half-spherical cross-section, and a generally planar flange portion 30 extending in a plane outwardly of the main, neck and head portions and sealed to said top surface 18 of the backing sheet 16, preferably by means of a vacuum seal formed by heat and pressure. The main, neck and head portions extend outwardly of top surface 18, and bound therewith a compartment 32 in which the pellets 12 are contained with clearance.

The packet 34 is provided with a frangible zone 34 which, when broken, enables removal of the pellets 12 from the compartment 32. In a preferred embodiment, the frangible zone 34 extends across the neck portion 26 at the juncture between the neck and head portions, i.e., where the covering member has its smallest cross-section.

As previously mentioned, the backing sheet has a certain degree of frangibility and is bendable when subjected to external forces at the neck portion. The covering member has a degree of rigidity and, hence, frangibility greater than that of the backing sheet so that the covering member fractures at the neck portion when external forces, e.g., fingertip pressure, bend the backing sheet. Indeed, in use, the synthetic plastic material of the covering member does not substantially exhibit plastic deformation, but, instead, cracks open, whereas, the paper backing sheet merely creases. The covering member actually cracks into two fractured parts, both of which remain attached to the bent backing sheet due to the presence of the flange portion 30. Once cracked open, the frusto-conically-shaped neck portion has tapered walls bounding a pouring spout through which the pellets may pass for administration of the pharmaceutical preparation. The light-transmissive covering member permits the patient to view the pellets through the covering member to evaluate how many of the pellets have been removed from the compartment.

Figure 4:
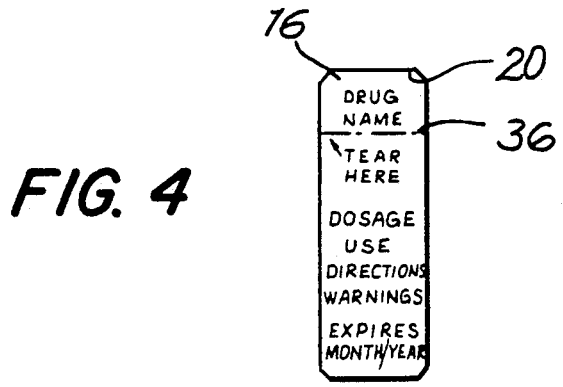
FIG. 4 is a rear view of the arrangement of FIG. 1, bearing printed indicia.

The juncture between the neck 26 and the head 28 portions of the covering member is sufficient, due to its reduced cross-section, to constitute the frangible zone at which the covering member is fractured. In some cases, it may be desirable to facilitate the breaking operation by further weakening the frangible zone by providing a crease line across the rear of the backing sheet 16 immediately behind the aforementioned juncture. As shown in FIG. 4, the crease line can also be constituted by a series of linear perforations 36, none of which goes entirely through the backing sheet in order to maintain the integrity and seal of the compartment 32.

Also shown in FIG. 4 is a set of exemplary indicia applied, e.g., by printing, onto the bottom surface 20 of the backing sheet 16. The indicia may include the identification of the drug, instructions as to how to break open the packet, the dosage amount of the pharmaceutical preparation within the packet, directions for use, the expiration date, a warning notice, and any other information which the drug manufacturer wishes to impart to the patient. The indicia need not be applied only to the bottom surface 20 of the backing sheet; they could equally as well be applied to the front surface thereof, or to the covering member.

Figure 5:
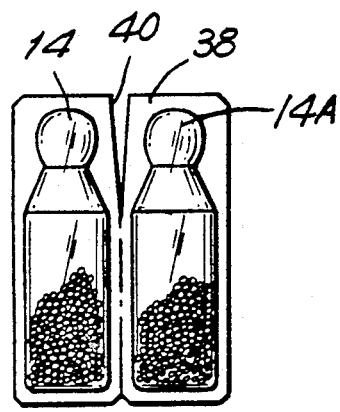
FIG. 5 is a top plan view of another arrangement for administering a pharmaceutical preparation in accordance with this invention.

As shown in FIG. 5, more than one breakable packet can be attached to the same backing sheet. Thus, packets 14, 14A are both provided on a backing sheet 38 in an analogous manner to that described earlier for backing sheet 16, except that the backing sheet 38 is provided with a V-shaped notch 40 to permit ready detachment of each packet from the backing sheet 38 by tearing along the notch 40. Alternatively, each of the packets 14, 14A may be separately opened for removal of the pellets by rupturing the juncture between the neck 26 and head 28 on each packet when desired, without separation of the backing sheets of the joined packets.

This invention also contemplates the provision of more than two packets on a single backing sheet 38 and, indeed, the packets can be mounted on a continuous strip wound in a roll, or on a large sheet, each packet being detachable from the strip by any convenient tear-off means, or being separately rupturable for removal of the pelletized medication.

Figure 3:
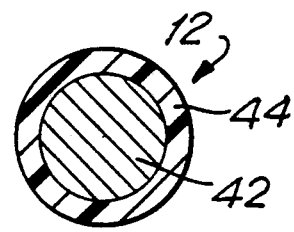
FIG. 3 is a greatly enlarged sectional view of one of the multitude of pellets containing the pharmaceutical preparation.

Turning, then, to FIG. 3, each pellet contains a core 42 of a pharmaceutical preparation comprising one or more active ingredients, and pharmaceutically acceptable excipients, binders and fillers, if any, as well as a non-tacky outer coating 44. Each pellet has an average total diameter of not greater than 1 mm. Each non-tacky coating includes a polymeric material, which advantageously comprises a polymer which is a cationic copolymeric acrylic resin based on methacrylate and neutral methacrylic acid esters, and a basic compound filler. An example of such cationic copolymeric acrylic resin is "EUDRAGIT E" (Pharma International).

As a basic compound, any organic or inorganic compound having a high degree of solubility in an acidic medium may be used and, as preferred embodiments, calcium carbonate, aluminum hydroxide or magnesium carbonate may be mentioned. The filler is preferably present in an amount from about 10% to about 90% by weight of the coating, preferably in a range from about 30% to about 60% by weight and, still more preferably, in amount about 50% by weight. The filler reduces the amount of polymer that is used, greatly reducing manufacturing costs. The filler reduces the tackiness of the polymer to not only reduce manufacturing difficulties in coating, but also promotes the dissolution of the pellets in the gastric juices of a patient's stomach, as heretofore described.

A major purpose of the coating is also to mask the taste of the pharmaceutical preparation in the cores of the pellets and, accordingly, to delay the dissolution of the pellets until they have reached the patient's stomach.

Another embodiment of this invention involves utilizing as the polymeric material in the pellet coating a water-soluble polymer such as gelatin or hydrogel compounds. Examples of such water-soluble polymers are acrylamide, N-vinyl pyrolidone and N,N'-methylenebisacrylamide.

The pharmaceutical preparation itself can comprise any orally-active, gut-absorbably active ingredient including, by way of example, analgesics, such as acetaminophen, aspirin, ibuprofen, morphine; antiasthmatics, such as theophylline, albuterol, prednisone, prednisolone; antimicrobials (antibacterials, antibiotics, antifungal agents), such as sulfa drugs, trimethoprim, nitrofurantoin, penicillins, cephalosporins, tetracyclines, chloramphenicol, erythromycin, griscofulvin, nystatin; antihistamines, such as phenylpropranolamine, pseudoephedrine, clemastine, terfenadine; anti-inflammatory agents, such as phenylbutazones, salicylates, steroids, naproxen, piroxicam, indomethacin, ketoprofen, sulindac; antiepileptic agents, such as valproic acid, carbamazepine; cough and cold medicines, such as dextromethorphen, guaifenesin, chlorphenitamine, ammonium chloride; cardiovascular agents, such as labetolol, propranolol, timolol, verapamil, diltiazem, nifedipine, procainamide, guinidines; diuretics, such as furosemide, thiazides, spironolactone; laxatives, such as docusate, bisacodyl; tranquilizers, such as lorazepam, prazepam, diazepam, chlordiazepoxide, hydroxyzine, meprobamate, phenothiazines; vitamins.

The backing sheet need not be constituted solely of paper, but may be coated with a plastic or aluminum layer.

In practice, the novel pharmaceutical dispensing arrangement is provided to a health professional or to the patient who administers the pharmaceutical preparation by rupturing one or more of the individual dosage packets and pouring the contents into the mouth of the patient for immediate swallowing, with or without water or other accompanying liquid. The pellets would normally be self-administered into the mouth, except in the case of small children, elderly or incapacitated patients, or drug addicts, psychiatric patients and others who may conceal or not take their medication if self-administration is permitted.

It will be understood that each of the elements described above, or two or more together, also may find a useful application in other types of constructions differing from the types described above.

While the invention has been illustrated and described as embodied in an arrangement for, and method of, administering a pharmaceutical preparation, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

I claim:

1. An arrangement for administering a pharmaceutical preparation, comprising:
   a multitude of pellets containing a pharmaceutical preparation and having non-tacky coatings; and
   a breakable packet including a backing sheet having opposite major planar surfaces, and a covering member overlying the backing sheet, and extending outwardly of, and having a flange portion sealed to one of said major surfaces, said covering member bounding with the backing sheet a compartment in which the pellets are contained, said covering member including a hollow main portion having a predetermined half-cylindrical cross-section and extending along a longitudinal direction, a neck portion having a half-frusto-conical cross-section less than said predetermined cross-section and tapered walls which converge toward each other along the longitudinal direction to a waist, and a head portion having a half-spherical cross-section and tapered walls which diverge apart along the longitudinal direction away from the waist, said covering member having its smallest dimension, as considered along a transverse direction generally perpendicular to the longitudinal direction, at the waist, said packet having across the waist a frangible zone which, when broken, forms the neck portion as a tapered pouring spout through which the pellets are poured from the compartment.

2. The arrangement as recited in claim 1, wherein the covering member has a predetermined degree of frangibility, and wherein the backing sheet has a degree of frangibility less than said predetermined degree of frangibility.

3. The arrangement as recited in claim 2, wherein the backing sheet is constituted of a paper material coated with plastic or aluminum, and wherein the covering member is constituted of a synthetic plastic material.

4. The arrangement as recited in claim 1, wherein the pharmaceutical preparation comprises an active ingredient and pharmaceutically acceptable binders, fillers or excipients.

5. The arrangement as recited in claim 4, wherein said active ingredient is orally active.

6. The arrangement as recited in claim 1, wherein the backing sheet is bendable when subjected to external forces at the waist, and wherein the covering member fractures at the waist when said external forces bend the backing sheet.

7. The arrangement as recited in claim 6, wherein the covering member fractures into fractured parts which remain attached to the bent backing sheet, one fractured part being the head portion, and another fractured part being the main and neck portions.

8. The arrangement as recited in claim 5, wherein said orally active ingredient is selected from the group consisting of analgesics, antiasthmatics, anti-microbials, antibacterials, antibiotics, antifungal agents, antihistamines, anti-inflammatory agents, antiepileptic agents, cough and cold medicines, cardiovascular agents, diuretics, laxatives, tranquilizers, and vitamins.

9. The arrangement as recited in claim 1, wherein the covering member is constituted of a light-transmissive material to permit viewing of the pellets through the covering member.

10. The arrangement as recited in claim 1, wherein the packet includes indicia applied onto the other of said major surfaces of the backing sheet.

11. The arrangement as recited in claim 1; and further comprising another covering member overlying the backing sheet and bounding therewith another compartment in which additional pellets are contained.

12. The arrangement as recited in claim 1, wherein each pellet has a diameter not greater than 1 mm, said pellets being freely accommodated with clearance in the compartment.

13. The arrangement as recited in claim 1, wherein each non-tacky coating includes a polymeric material.

14. The arrangement as recited in claim 13, wherein each non-tacky coating further includes a basic compound filler that is soluble in acid.

15. The arrangement as recited in claim 13, wherein the polymeric material includes a cationic copolymeric acrylate resin based on methacrylate and neutral methacrylic acid esters.

16. The arrangement as recited in claim 14, wherein the basic compound filler is selected from the group consisting of calcium carbonate, aluminum hydroxide and magnesium carbonate.

17. The arrangement as recited in claim 14, wherein the basic compound filler is present in the coating in an amount from about 10% to about 90% by weight.

18. The arrangement as recited in claim 13, wherein the polymeric material is selected from the group consisting of cellulosic, polyacrylate and polyvinyl-alcoholic polymers.

19. The arrangement as recited in claim 1, wherein the pharmaceutical preparation contained in the pellets is a fraction of a dose to be administered to a human patient.

20. The arrangement as recited in claim 1, wherein the pharmaceutical preparation contained in the pellets is a multiple of a dose to be administered to a human patient.

21. A method of administering an orally active pharmaceutical preparation to a patient, comprising the steps of:
   (a) breaking open a frangible packet having a backing sheet having opposite major planar surfaces, and a covering member overlying the backing sheet, and extending outwardly of, and having a flange portion sealed to one of said major surfaces, said covering member bounding with the backing sheet a compartment, said compartment housing non-tacky coated pellets containing the preparation, said covering member including a hollow main portion having a predetermined half-cylindrical cross-section and extending along a longitudinal direction, a neck portion having a half-frusto-conical cross section less than said predetermined cross-section and tapered wall which converge toward each other along the longitudinal direction to a waist, and a head portion having a half-spherical cross-section and tapered walls which diverge apart along the longitudinal direction away from the waist, said covering member having its smallest dimension, as considered along a transverse direction generally perpendicular to the longitudinal direction, at the waist, said breaking open step being performed by breaking the packet across the waist to form the neck portion as a tapered pouring spout; and
   (b) pouring the pellets from the tapered pouring spout into a human or animal patient's mouth.

* * * * *